(12) United States Patent
Chappel et al.

(10) Patent No.: US 11,819,662 B2
(45) Date of Patent: Nov. 21, 2023

(54) MEMS FLUID PUMP WITH INTEGRATED PRESSURE SENSOR FOR DYSFUNCTION DETECTION

(71) Applicant: DEBIOTECH S.A., Lausanne (CH)

(72) Inventors: Eric Chappel, Saint-Julien-en-Genevois (FR); Niklaus Schneeberger, Lausanne (CH); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 1033 days.

(21) Appl. No.: 16/422,668

(22) Filed: May 24, 2019

(65) Prior Publication Data

US 2019/0368484 A1 Dec. 5, 2019

Related U.S. Application Data

(62) Division of application No. 14/949,460, filed on Nov. 23, 2015, now Pat. No. 10,316,836, which is a
(Continued)

(51) Int. Cl.
*A61M 5/168* (2006.01)
*A61M 5/36* (2006.01)
(Continued)

(52) U.S. Cl.
CPC ........ *A61M 5/16854* (2013.01); *A61M 5/168* (2013.01); *A61M 5/365* (2013.01);
(Continued)

(58) Field of Classification Search
CPC .. A61M 5/16854; A61M 5/168; A61M 5/365; A61M 5/14224;
(Continued)

(56) References Cited

U.S. PATENT DOCUMENTS

| 5,759,014 A | 6/1998 | Van Lintel |
| 7,104,763 B2 | 9/2006 | Bouton et al. |

(Continued)

FOREIGN PATENT DOCUMENTS

| EP | 1762263 A1 | 3/2007 |
| WO | 2007/113708 A1 | 10/2007 |

OTHER PUBLICATIONS

The First Office Action dated Sep. 6, 2015, issued in China Application No. 2013106811867 and English translation, 17 pages.

*Primary Examiner* — Jason E Flick
(74) *Attorney, Agent, or Firm* — Nixon & Vanderhye P.C.

(57) ABSTRACT

The invention relates to a pumping device including a pump (1) comprising—a pumping chamber (11) having a variable volume, —an inlet (2) communicating with the pumping chamber (11) and comprising a valve, —an outlet (5) communicating with the pumping chamber and comprising a valve, —an actuator adapted to change the volume of the pumping chamber, —a fluidic pathway comprising said inlet (2), said pumping chamber (11), said outlet (5) and a downstream line (7) situated downstream of the outlet valve, —a pressure sensor (4) for measuring the pressure between the valves of said pathway, —processing means for processing the received pressure data from the pressure sensor (4). The invention also covers a method for detecting a dysfunction in a pumping device as defined above.

13 Claims, 15 Drawing Sheets

Related U.S. Application Data division of application No. 13/059,507, filed as application No. PCT/IB2008/054353 on Oct. 22, 2008, now Pat. No. 9,192,720.

(51) Int. Cl.
- *A61M 5/142* (2006.01)
- *F04B 43/04* (2006.01)
- *F04B 51/00* (2006.01)

(52) U.S. Cl.
CPC .................. *A61M 5/14224* (2013.01); *A61M 2005/16863* (2013.01); *A61M 2005/16868* (2013.01); *A61M 2205/0244* (2013.01); *A61M 2205/0294* (2013.01); *A61M 2205/3355* (2013.01); *A61M 2205/70* (2013.01); *F04B 43/043* (2013.01); *F04B 51/00* (2013.01)

(58) Field of Classification Search
CPC ......... A61M 2005/16863; A61M 2005/16868; A61M 2205/3355; A61M 2205/70; A61M 5/14; A61M 5/16831; A61M 5/16859; A61M 2005/16872; A61M 5/1723; A61M 2005/1726; A61M 2205/33; A61M 2205/3331; A61M 2205/702; A61M 5/142; A61M 5/14212

See application file for complete search history.

(56) References Cited

U.S. PATENT DOCUMENTS

| | | | |
|---|---|---|---|
| 9,192,720 B2* | 11/2015 | Chappel | A61M 5/16854 |
| 2008/0214979 A1 | 9/2008 | Brugger et al. | |
| 2008/0234630 A1* | 9/2008 | Iddan | A61M 5/16809 604/48 |
| 2019/0314575 A1* | 10/2019 | Wilcox | A61M 5/14248 |

\* cited by examiner

MEMS FLUID PUMP WITH INTEGRATED PRESSURE SENSOR FOR DYSFUNCTION DETECTION

This application is a divisional of U.S. patent application Ser. No. 14/949,460 filed Nov. 23, 2015 (U.S. Pat. No. 10,316,836), which is a divisional of Ser. No. 13/059,507 filed Feb. 17, 2011 (U.S. Pat. No. 9,192,720), which is the U.S. national phase of International Application No. PCT/IB2008/054353 filed Oct. 22, 2008, which designated the U.S., the entire contents of each of which are hereby incorporated by reference.

TECHNICAL FIELD

The present invention relates to medical pumping devices and more precisely to the detection of dysfunctions in such devices.

BACKGROUND ART

The detection of dysfunctions, especially in medical devices, is important because the life of the patient may depend on proper functioning of said devices. In case of infusion pumps, for example, the potentially dangerous results of a failure are typically over-infusion or under-infusion of the drug into the patient.

Examples of dysfunctions are leaks, occlusions or presence of air bubbles in the pumping line.

State-of-the-art devices and methods for detecting dysfunctions in medical devices are for instance disclosed in the following patent documents US 2008/214979, EP 1 762 263 and U.S. Pat. No. 7,104,763.

When using certain drugs, such as insulin, the detection of occlusion may be of particular importance since it is known that catheters may occlude in numerous circumstances. Any such undetected occlusion may result in under-delivery of insulin because it remains undetected for a long period of time. Current occlusion detection devices operate on the piston of the syringe driver and need the building of high pressure inside the syringe before it is detected. Other occlusion detectors consist of pressure sensors situated after the pumping mechanism, on the patient line, which have little sensibility because of e.g. the compliance factor of the tubing line. In certain cases, the absence of detection of an occlusion at the onset of such occlusion result in a high glucose plasma concentration which may appear to the patient as a need to increase its insulin level, resulting in a re-programming of the pump which may result, in the event the occlusion would be suddenly released, in a larger quantity of insulin being suddenly administered with potential serious hazard to the patient.

SUMMARY OF THE INVENTION

The present invention offers an alternative and several improvements with respect to state-of-the-art devices and methods.

In the invention, the detection of a dysfunction is based on the measurement of the pressure in the pumping line and more precisely between the inlet and outlet valve of the pumping chamber.

Such a configuration offers a higher sensitivity as well as the potential to detect several potential kinds of dysfunction.

More specifically the invention relates to a pumping device and to a related method as defined in the claims.

According to a preferred embodiment of the invention, the inlet and outlet of the pumping device include passive valves.

Advantageously, in the scope of the present invention (but not limited thereto), a highly miniaturized infusion pump is considered. It is a membrane pump with two passive valves and is built using MEMS technology. In contrast to syringe driven pumps, a silicon micro-pump and preferably such micro-pumps are build from silicon, exhibits a more complex fluidic pathway and more precise control of the delivery while including valves with a hard seat which may potentially be leaking in the presence of particles.

A further preferred embodiment of the invention uses a pressure sensor which comprises a silicon membrane.

In another advantageous of the invention, the pressure sensor is placed between the pumping chamber and the outlet. This configuration offers a more precise control of the occlusion (including the potential to detect immediately the onset of an occlusion during any pumping cycle) while addressing other purposes such as the detection of dysfunctions.

According to another preferred embodiment of the invention the system comprises a further pressure sensor (12).

This further pressure sensor (12) may be preferably placed after the outlet valve, in the downstream line. The further pressure sensor (12) can be positioned between the outlet valve and the flow restrictor (13).

In some embodiments the system also comprises a temperature sensor.

The pressure sensor according to the invention may detect several types of dysfunctions such as occlusions, air bubbles or infusion line disconnection, generally during a very short time, i.e. a few seconds, when the pump is operating.

Another objective of the present invention is to precisely characterize and/or monitor the characteristics of a pump during the manufacturing cycle to prevent any potential malfunction during use.

It is an objective for the manufacturing of any medical device, to ensure the quality of each pump delivered to a patient. For any such medical product, the use of liquid is generally the only way to detect a malfunction of a pump. While such a test requires a long time and represents a significant cost, it is only possible if the entire fluidic line is changed after such test. In the event of a single use product (such as a disposable pump), it is not possible to change the fluidic line and therefore it is not possible to ensure a 100% testing of each such pump manufactured, due to the liquid contamination during testing. Only a sampling of a batch can therefore be operated, such testing being destructive for the pumps considered, without insuring a 100% quality control.

The present also provides a system and a method which allows for a complete control of each pump produced without resulting in a contamination of such pump. Such testing is preferably carried out with filtered air and results in a detailed analysis of all important parameters and safety characteristics in a very short period of time of only a few seconds—This way remains compatible with the cost objectives of such disposable pumps which need to remain very inexpensive to manufacture.

DETAILED DESCRIPTION OF THE INVENTION

The invention will be better understood below with a detailed description including examples illustrated by the following figures.

Figure 15:
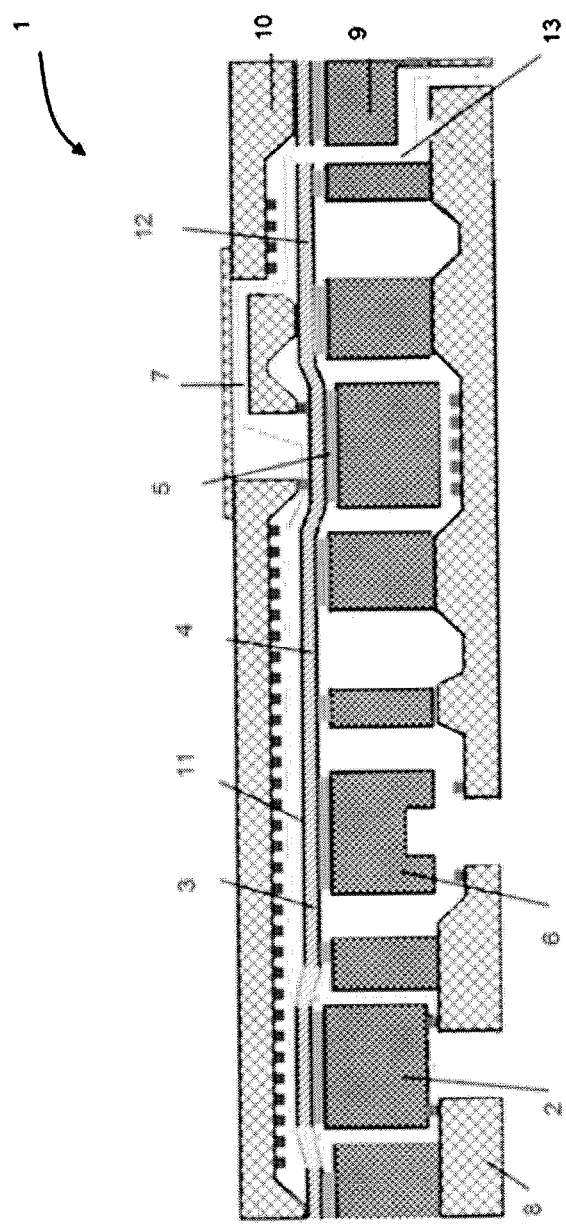
FIG. 15 shows a cut view of a micro-pump according to an embodiment of the invention.
Figure 16:
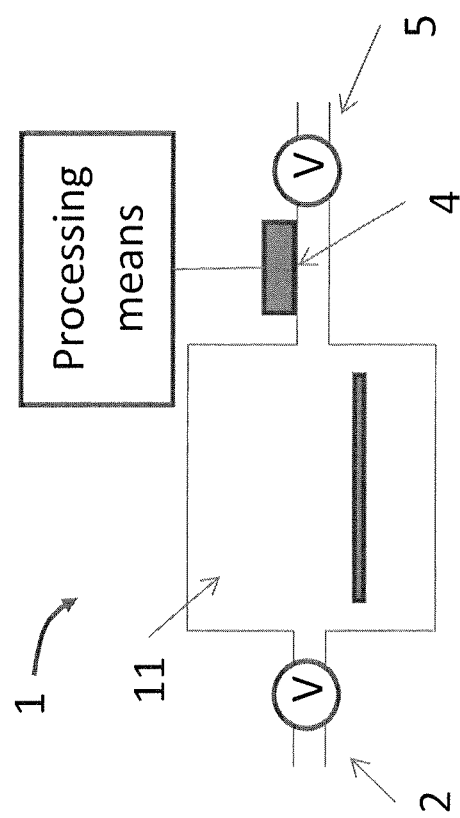
FIG. 16 illustrates valve, chamber, and processing portions of the invention.

In summary, with reference to the Figures (e.g., FIGS. 1, 15, and 16), the invention relates to a pumping device including a pump (1) comprising:

a pumping chamber (11) having a variable volume, an inlet (2) communicating with the pumping chamber (11) and comprising an inlet valve, an outlet (5) communicating with the pumping chamber and comprising an outlet valve, an actuator adapted to change the volume of the pumping chamber, a fluidic pathway comprising said inlet (2), said pumping chamber (11), said outlet (5) and a downstream line (7) situated downstream of the outlet valve, a pressure sensor (4) for measuring the pressure between the valves of said pathway, processing means for processing the received pressure data from the pressure sensor (4).

The invention also covers a method for detecting a dysfunction in a pumping device as discussed above.

Micro-Pump

Figure 1:
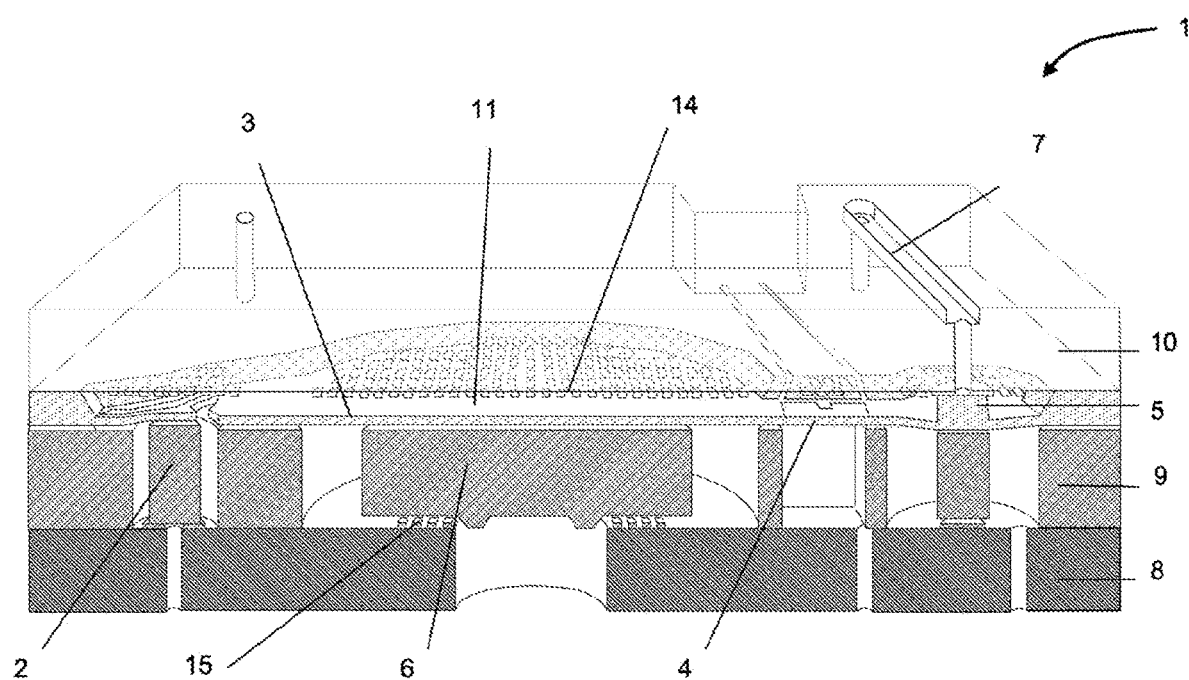
FIG. 1 shows a cut view of a micro-pump according to a preferred embodiment of the invention.

The micro-pump 1 as illustrated in FIG. 1 is a highly miniaturized and reciprocating membrane pumping mechanism. It is made from silicon and glass, using technologies referred to as MEMS (Micro-Electro-Mechanical System). It contains an inlet control member, here an inlet valve 2, a pumping membrane 3, a functional detector 4 which allows detection of various failures in the system and an outlet valve 5. The principle of such micro-pumps is known in the prior art, for example from U.S. Pat. No. 5,759,014.

FIG. 1 illustrates a pump with the stack of a glass layer as base plate 8, a silicon layer as second plate 9, secured to the base plate 8, and a second glass layer 10 as a top plate, secured to the silicon plate 9, thereby defining a pumping chamber 11 having a volume.

An actuator (not represented here) linked to the mesa 6 allows the controlled displacement of the pumping membrane 3. A channel 7 is also present in order to connect the outlet control member, the outlet valve 5 to the outlet port placed on the opposite side of the pump.

Detector Principle

In the pump 1, the pressure inside the pumping chamber varies during a pumping cycle depending on numerous factors, such as the actuation rate, the pressure at the inlet and the outlet, the potential presence of a bubble volume, the valve characteristics and their leak rates.

According to the invention, it is the intent to monitor this pressure and to analyse the profile from one stroke to another in order to detect potential dysfunctions.

Integrated Pressure Sensor

The pressure sensor 4 in the micro-pump 1 is made of a silicon membrane placed between the pumping chamber and the pump outlet. It is located in a channel formed between the surface of the micro-pumps silicon layer and its top glass layer. In addition, it comprises a set of strain sensitive resistors in a Wheatstone bridge configuration on the membrane, making use of the huge piezo-resistive effect of the silicon. A change of pressure induces a distortion of the membrane and therefore the bridge is no longer in equilibrium. The sensor is designed to make the signal linear with the pressure within the typical pressure range of the pump.

The fluid is in contact with the surface of the interconnection leads and the piezo-resistors. A good electrical insulation of the bridge is ensured by using an additional surface doping of polarity opposite to that of the leads and the piezo-resistors.

In another preferred embodiment of the invention the pressure sensor includes an optical sensor. The sensor is preferably composed of one part which is included in the pathway of the pump in-between the two vales and at least some optical parts placed outside of such fluidic pathway and able to measure the pressure detected inside the fluidic pathway. In another embodiment, the optical detection may also be placed entirely inside the pump while being able to measure the pressure in-between the two valves in the fluidic pathway. In another embodiment, an optical astigmatic element is located within the light path, i.e. between a flexible membrane in the pump and the optical sensor. Any change of pressure in the pump induces a displacement of said membrane, a change of the light path and thus a change of the optical beam shape thanks to the presence of the astigmatic element. The optical sensor is preferably sensitive to the shape of the optical beam, e.g. by including a quadrant photodetector.

Functional Test

A first process that can be carried out with the pump according to the present invention is a functional test of said pump, e.g. at the manufacturing level.

While known functional tests using water last several hours and must be considered as destructive, the functional testing of the pump according to the present invention can be done in few seconds only with gas. To this effect, one uses the tiny dead volume of the pump for this test and the integrated pressure sensor described above.

The principle of this functional test process is the following: an overpressure is created inside the pump with the actuator and one monitors the pressure decay in the pumping chamber which is directly indicative of the leak rate. The maximum pressure is related to the compression ratio of the pump and its self-priming capability. One can also derive the valve pretension during a typical actuation cycle.

Figure 2:
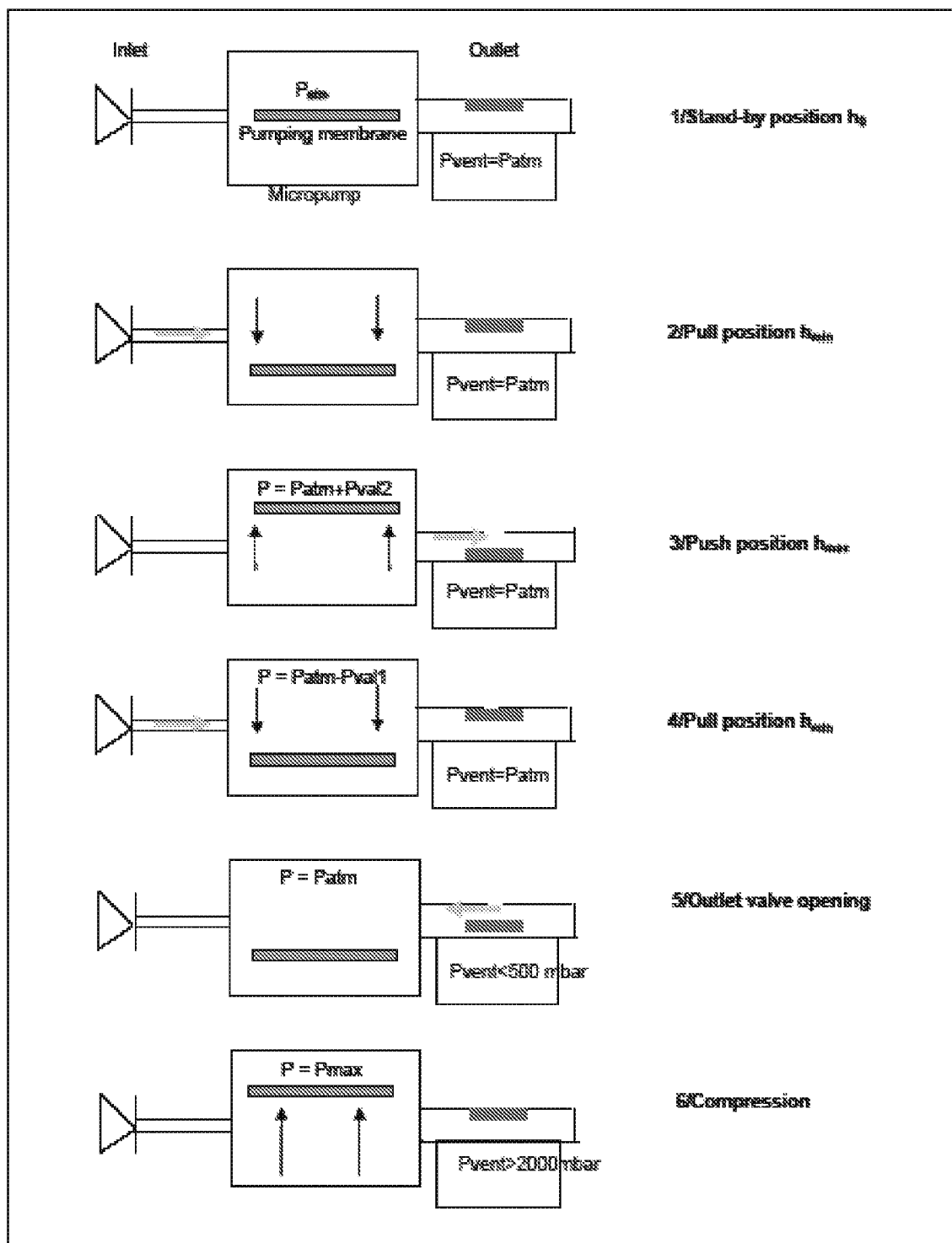
FIGS. 2 and 3 illustrate a possible process of functional testing of the pump.
Figure 3:
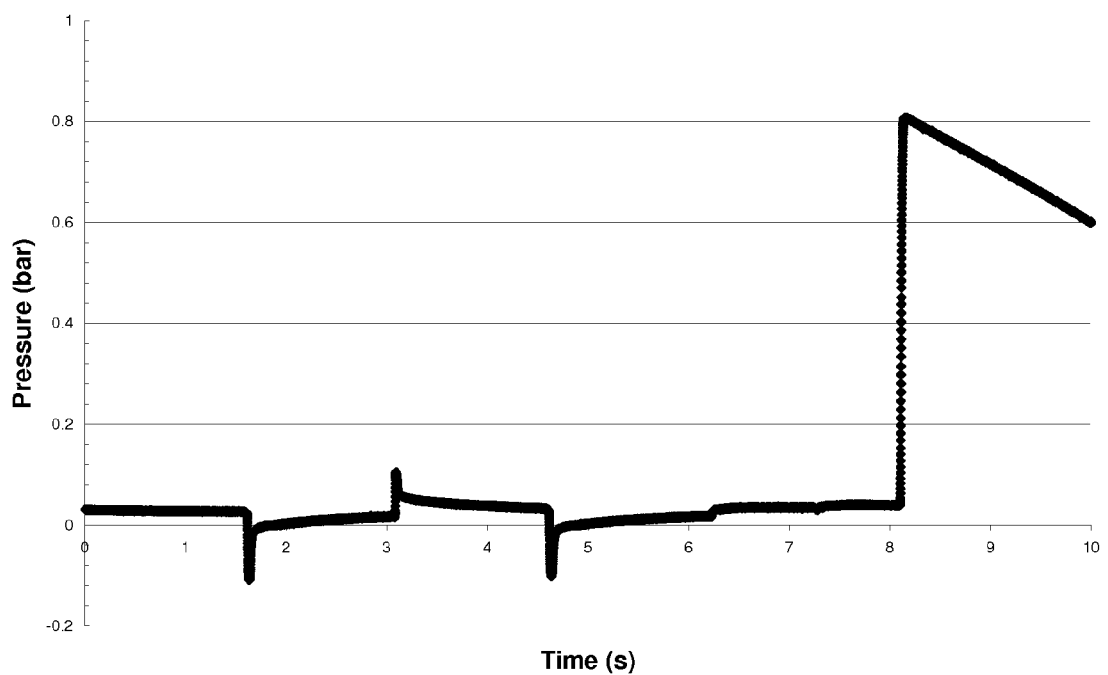

To generate the high pressure in the chamber one can control the outlet valve, e.g. pneumatically, in order to keep it closed during the compression as shown in FIGS. 2 and 3.

More specifically FIGS. 2 and 3 represent the functional testing of the pump according to the present invention (in FIG. 2 the schematic process and in FIG. 3 the corresponding pressure profile).

During this test one monitors the signal of the detector whereby:

Pressure=0 indicates the rest position of the membrane

The pressure peak indicates the compression ratio of the micro-pump

The pressure decay indicates the leakage rate of the valves

The pressure in the step 3 indicates the pretension of the outlet valve

The pressure in the step 4 indicates the pretension of the inlet valve

As illustrated (see for example the successive positions in FIG. 2), such test is started from a stand-by position. A pull step is first executed which "aspirates" gas into the chamber from the inlet valve 2 by movement of the membrane 3.

This is followed by a push step to empty the chamber of the gas, while the outlet valve 5 is open. In the next step, the outlet valve 5 is again closed and one carries out a further pull step with the membrane 3, and then in the next step one opens the outlet valve 5 to relief the under pressure in the chamber.

Finally, with the outlet valve 5 closed, one executes a push step which corresponds to a compression step with the membrane 3. The chamber is now under high pressure and the pressure decay (see FIG. 3) is an indication of the leakage rate of the valves.

The sensitivity of the method is very high due to the high pressure generated and the tiny volume involved.

A direct correlation between the compression ratio and the stroke volume SV is found if one assumes that dead volume DV does not vary too much thanks to a suitable process control during the initial manufacturing of the pump (e.g. by MEMS techniques).

Figure 4:
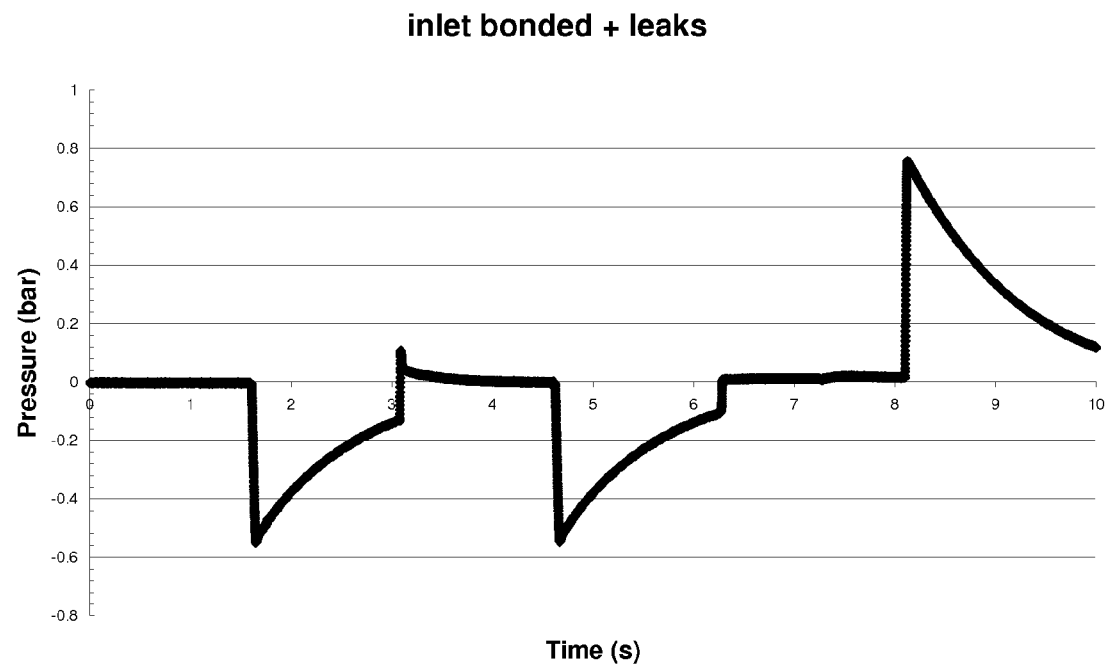
FIG. 4 illustrates another pressure profile of functional testing illustrating a dysfunction.

FIG. 4 illustrates the pressure profile in case of a failure of the functional test.

In this case, the inlet valve of the pump is bonded (maintained closed) and moreover there is a leakage. These problem related to the inlet valve can be deducted by the large under pressure created during the pull move of the pump and the decay of the pressure after each actuation. The leakage is indicated by the decay at the end of the high compression step, at the end of the test cycle.

The same result can also be obtained during the functioning of the pump in the event of a lack of fluid from the drug reservoir situated before the first valve (e.g. end of reservoir), in particular if using a closed soft reservoir with no air vent.

In-Line Dysfunction Detection

As mentioned previously, the pressure inside the pumping chamber while in fluid operation depends directly on various functional and/or external parameters, such as the pressure at the inlet or at the outlet, the actuation characteristics, but also micro-pump characteristics such as the valve tightness, the actual stroke volume or the valves pre-tension.

Figure 5:
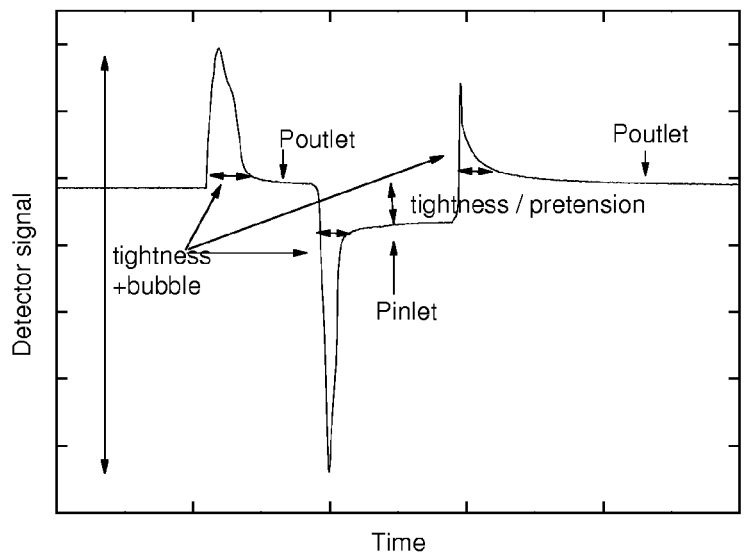
FIG. 5 illustrates a typical pressure profile during an actuation cycle.

A typical pressure profile during an actuation cycle with liquid is illustrated in FIG. 5.

Any change of this profile indicates a dysfunction of the pump or an increase or decrease of pressure at the inlet or at the outlet (e.g. due to a bad venting, an under-pressure or an over-pressure of a liquid reservoir, situated before the inlet valve or an occlusion after the outlet valve).

In particular, the position of the plateau just after the first peak of pressure measured inside the pumping chamber is a direct indication of the pressure at the outlet of the pump, after the outlet valve. After the second peak we have a direct indication of the pressure at the inlet, before the inlet valve. The tightness of the valves and/or the presence of bubbles induce a variation of the peak-to-peak amplitude and the peak widths. The analysis of the pressure decay after each peak of pressure indicates the leak rate of any of the valves.

Figure 6:
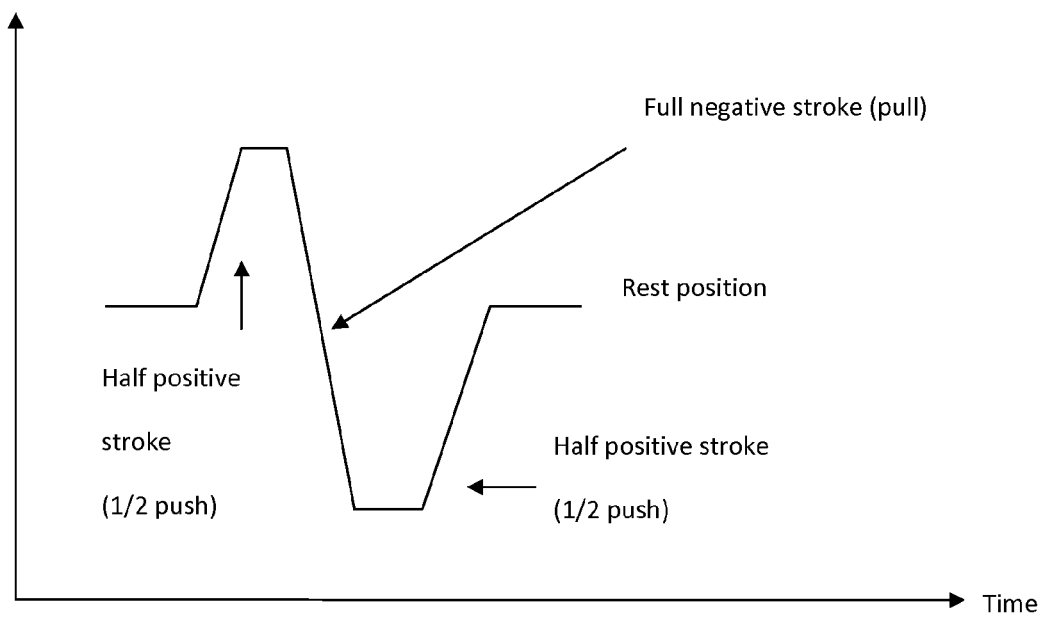
FIG. 6 illustrates one preferred embodiment of an actuation cycle.

The displacement of the membrane according to one embodiment of the invention during the normal actuation cycle of the pump is shown in FIG. 6.

According to such shown embodiment, the cycle is initiated by a first half push movement of the membrane, leading to an increase of the pressure, an opening of the outlet valve and therefore an exhaust of liquid.

The cycle is followed by a complete pull stroke in order to fill the pump (negative peak of pressure during the filling of the pump), and then the pumping membrane is released and therefore comes back to its rest position, inducing a second positive peak of pressure.

As said previously, the evolution of the pressure in the pumping chamber depends directly on the actuation characteristics of the membrane.

It is also possible, for instance, to have a cycle starting with a complete stroke, resulting from a full pull move first followed by a full push move. Such a cycle would typically be useful during a high speed operation of the pump, e.g. during a bolus administration. With an actuation like this only two peaks can be measured, a negative peak first and then a positive one. The analysis can be correlated to the actuation profile and result in the same kind of dysfunction detection.

As a consequence, the following features can always be measured during a pumping cycle by use of the pressure signal from the sensor situated in-between the two valves and result in a direct indication of the following characteristics:

1. The position of the plateau (+) just after a positive peak (+) of pressure depends on the outlet valve pretension and the pressure at the outlet of the pump after the outlet valve.
2. The position of the plateau (−) just after a negative peak (−) of pressure depends on the inlet valve pretension and the pressure at the inlet of the pump before the inlet valve.
3. The tightness of the valves and therefore the leaks are correlated to the decay with time of the pressure after each peak.
4. The relative positions of the two plateaus are also directly correlated to the leak rate.
5. The height and the width of the peaks of pressure (positive of negative) are directly correlated to the presence of air in the pump.

Priming and Air Detection

Figure 7:
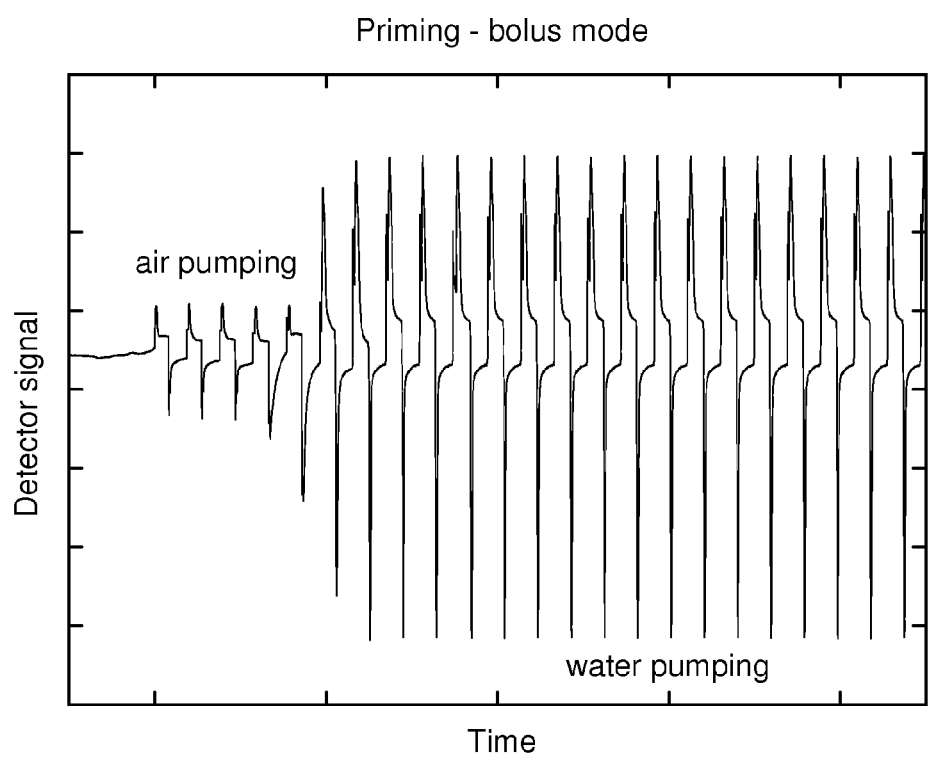
FIG. 7 illustrates pumping cycles of air and water.

The priming of the pump can also be monitored. The significant difference of signal observed during the pumping of air and water is illustrated in FIG. 7.

As discussed previously, the peaks of pressure are modified by the presence of air in the pump.

Air detection can be verified by:

1. Monitoring of the height of the peaks of pressure, resulting in a possible alarm at a given threshold.
2. Monitoring of the widths of the peaks of pressure, resulting in a possible alarm at a given threshold.

3. Monitoring of both heights and widths (via the integration of the signal for instance) resulting in a definition of an alarm threshold.

Outlet Pressure Monitoring

Figure 8:
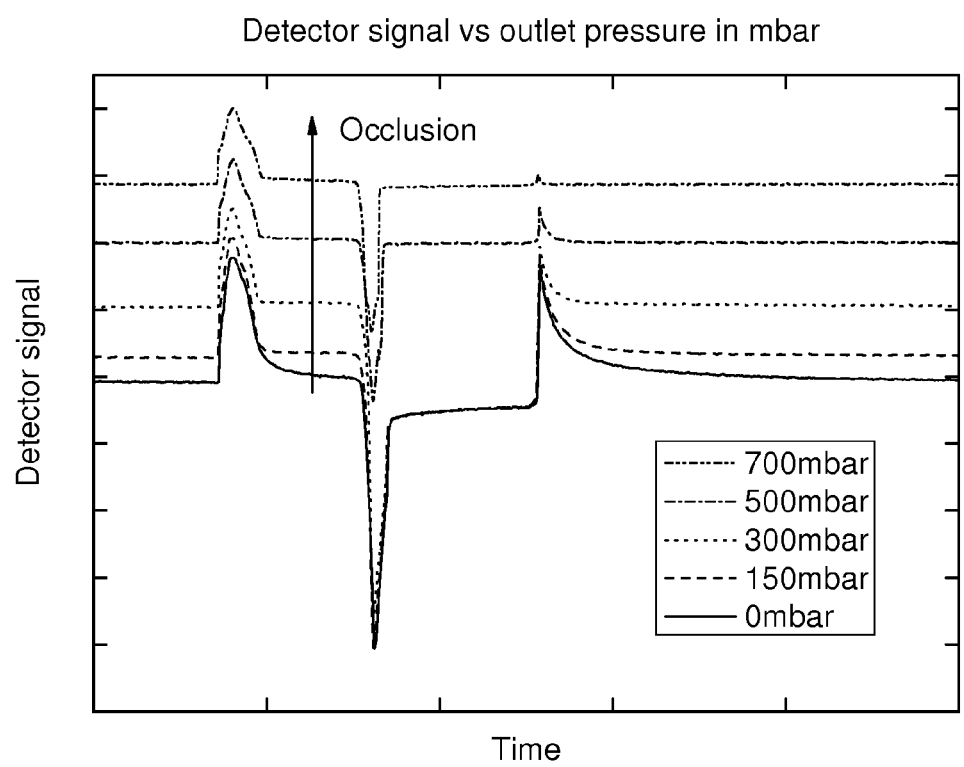
FIG. 8 illustrates a typical evolution of the outlet pressure profile in presence of an occlusion.

FIG. 8 shows a typical evolution of the pressure profile during an actuation in presence of pressure at the outlet of the pump after the outlet valve.

Inlet Pressure Monitoring

Figure 9:
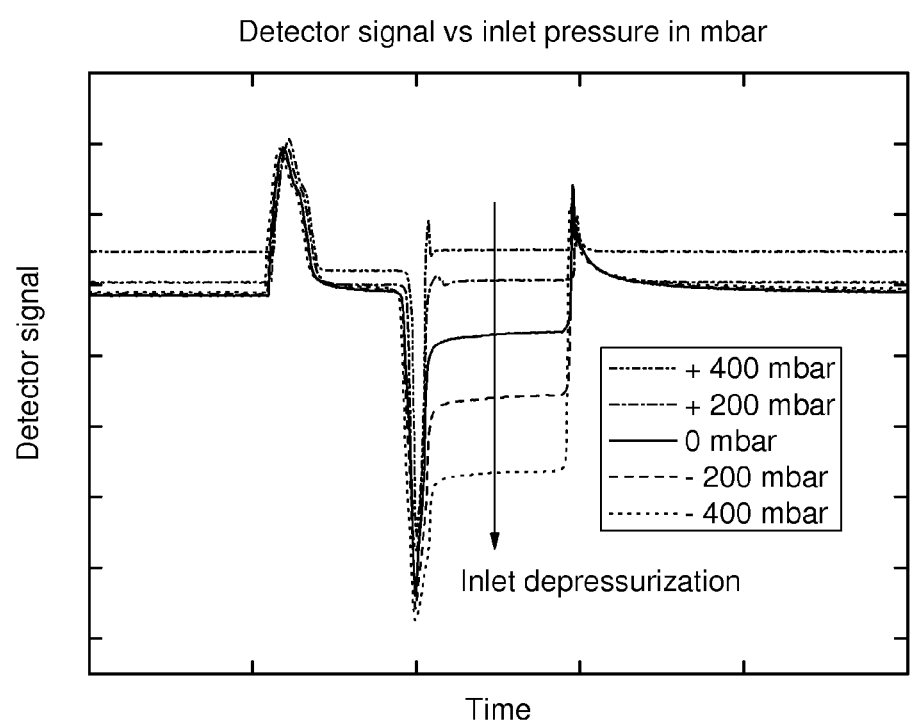
FIG. 9 illustrates a typical evolution of the inlet pressure profile in presence of an occlusion.

FIG. 9 shows the same graph as FIG. 8, with pressure at the inlet.

Accordingly, during an actuation cycle a precise monitoring of both inlet and outlet pressures can be obtained.

Such an inlet pressure monitoring can also help detecting the emptying of a drug reservoir, when such reservoir is e.g. a soft reservoir without air-vent.

Occlusion Detection

Figure 10:
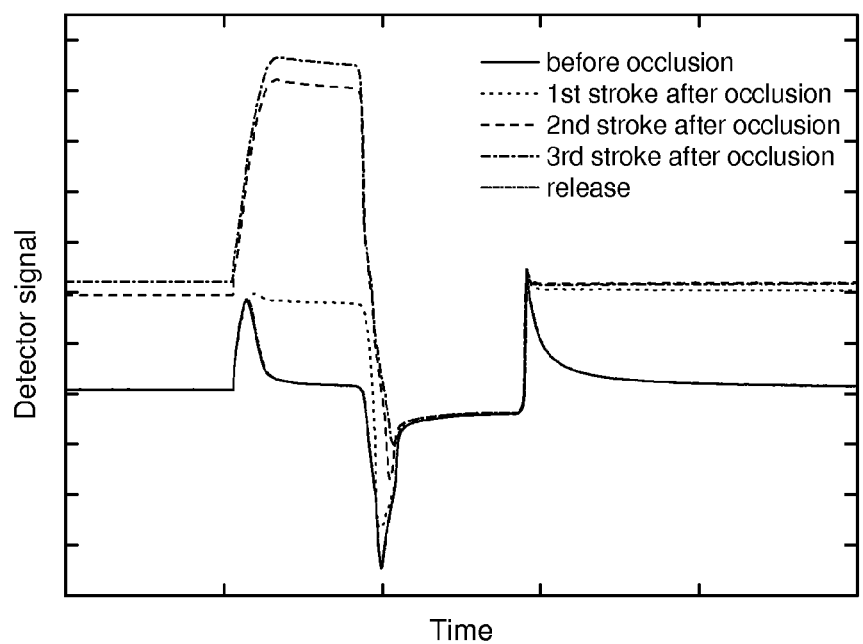
FIG. 10 illustrates an example of monitoring the outlet pressure during an occlusion.

The monitoring of the outlet pressure allows the occlusion detection as shown in FIG. 10.

There are several ways to analyse the curves reproduced in FIG. 10 during an occlusion. One can for instance simply observe the shift of the pressure after each push move.

Occlusion detection can be done by
1. Monitoring of the position of the plateau (+) and definition of an alarm threshold, typically when the position of the plateau (+) becomes equal to the initial height of the peak (+).
2. Monitoring of the height and the width of the peak (+) with an alarm threshold.

Figure 17:
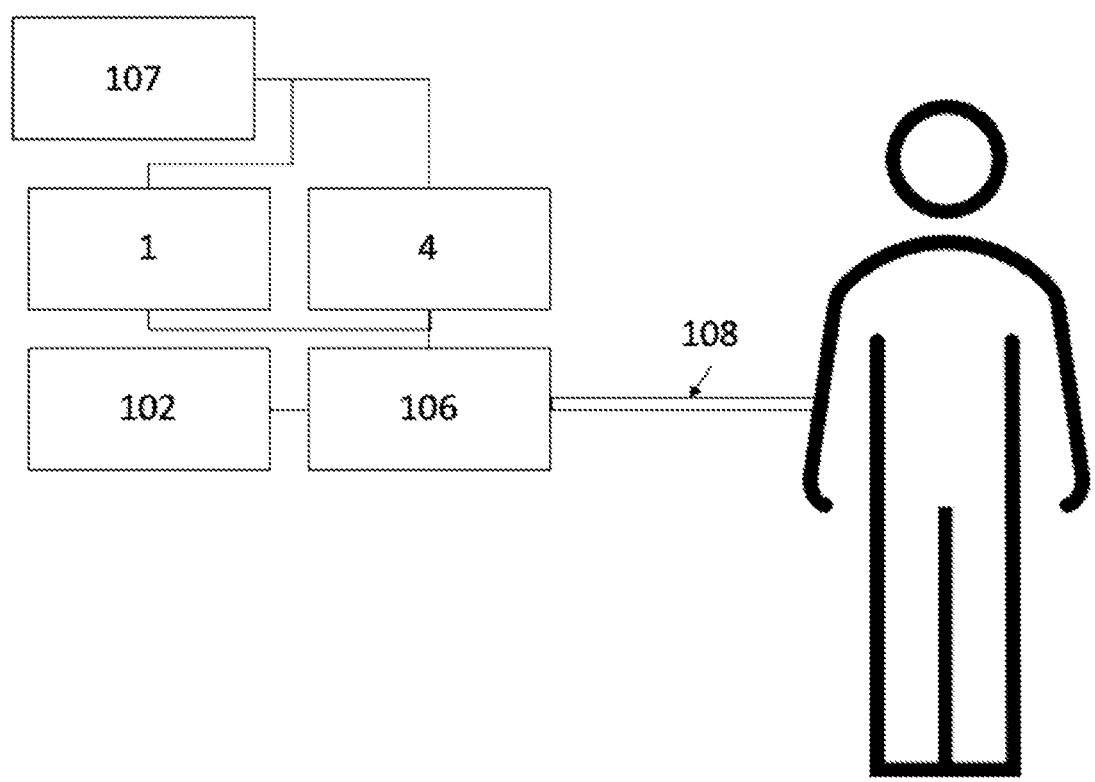
FIG. 17 shows a medical pumping system (101) comprising a reservoir (102) storing a medical fluid (103), a pump (1), a sensor (4) configured to measure the fluid pressure in the fluid pathway (106), a processor (107), and an infusion line (108) which injects the medical fluid at the injection site (109) of the patient (100).

Such a pressure measurement inside the pump 1 results in a very accurate and precise detection of an occlusion, since the measure is made inside the fluid pathway 106 and in correlation with other measured values indicative of other potential dysfunctions. Therefore, the resulting value measured can be correlated to the true occlusion or flow restriction outside the pump 1 and prevent any delay in informing the patient 100 of the need to either check the infusion line 108 or change the injection site 109. This is illustrated in FIG. 17.

Leakage Detection

Figure 11:
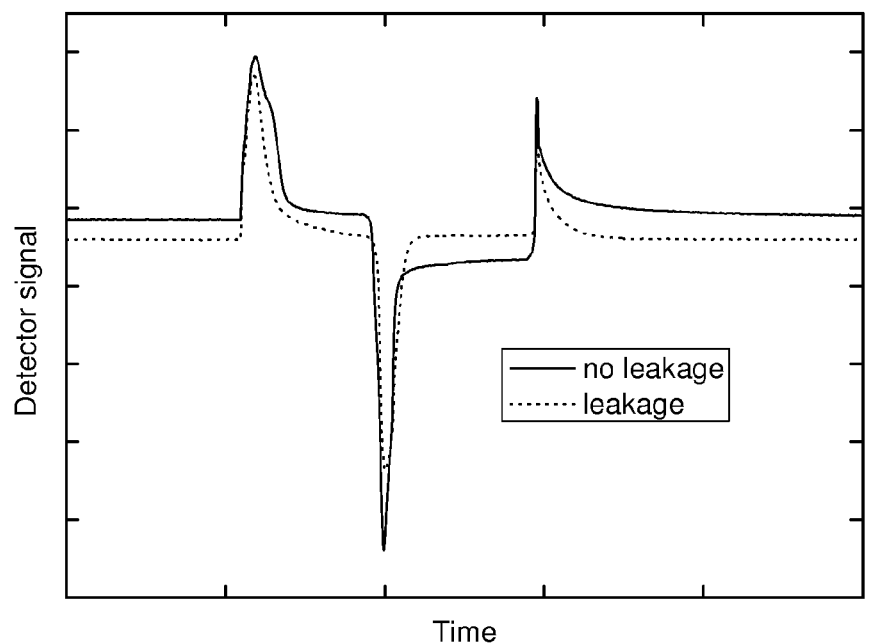
FIG. 11 illustrates a pressure profile of a pump with a presence of a leakage.

FIG. 11 illustrates the pressure profile of a pump with a leakage:

The pressure relaxes very quickly towards the external pressure after each actuation. Without leakage, the pressure should relax towards the valve pretension expressed in terms of pressure.

Accordingly, that valve pretension prevents free flow while also allowing leakage detection by the detection method of the present invention.

Figure 14:
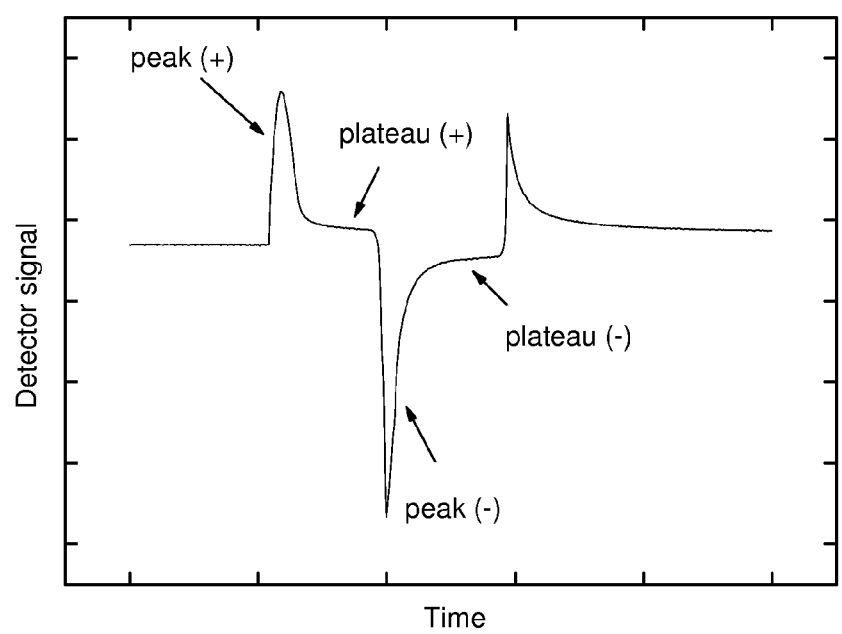
FIG. 14 shows how the definitions "peak" and "plateau" are used in the figures.

According to the notations given in the FIG. 14, leakage detection can be done by:
1. Monitoring of the relative positions of the plateau (+) and plateau (−) and definition of an alarm threshold.
2. Monitoring of the decay of pressure after each peak of pressure and definition of an alarm using typical time constant.

Monitoring of the Pumping Accuracy for Close-Loop Application e.g. with Insulin

With the invention, one is able to detect the failures such as valve leakage or air bubble that can affect the pumping accuracy within the accuracy specifications.

Figure 12:
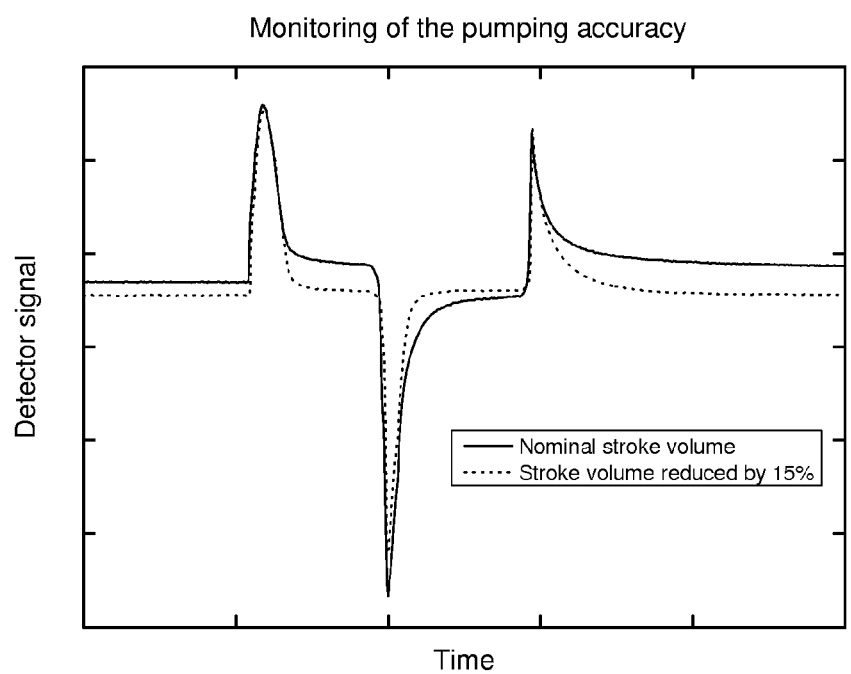
FIG. 12 illustrates a monitoring of pumping accuracy in the presence of a decrease of flow rate.

FIG. 12 illustrates an example of the detector signal of a pump showing a nominal stroke volume and the same pump with particles that affect the pumping accuracy by 15%. The leakage induced by these particles can be easily detected by analysing the difference of level before and after the large negative peak This feature allows close-loop application by coupling the micro-pump to a glucometer thanks to the control of the insulin delivery accuracy via the detector.

The detection here is similar to the leak detection, but the only focus is on leaks that affect the accuracy.
1. Monitoring of the relative positions of the plateau (+) and plateau (−) and definition of an alarm threshold, typically when they become equal after a typical time constant just after the peak (+) and (−).
2. Monitoring of the decay of pressure after each peak of pressure and definition of an alarm using typical time constant.

In the absence of such a precise monitoring of the accuracy of the pump, any such close loop system would result in increasing or decreasing the administration of e.g. insulin because of the measured parameter (in such case continuous monitoring of glucose level in e.g. the plasma or the subcutaneous region, or the interstitial fluid), without taking into account the alteration of the delivery of the pump. It is of upmost importance, in the case of a close loop system, to ensure that the pumping parameters are well understood and controlled over time to prevent any wrong compensation which would be related to the pumping mechanism and not the patient characteristics. In particular, an over infusion of insulin because of an increase of glucose measurement could potentially result in a hazard to the patient if related to an unknown defective pump or infusion set.

This is also particularly true when the glucose measurement is the reflect of a glucose plasma level within a 10 to 30 minutes delay. In such case, a defective pump would result in a wrong interpretation of the patient status, while any modification of the pump behaviour (e.g. infusion line occlusion relief or modification of the pumping characteristics) would not be detected in time to prevent hazard to the patient because of a such wrong interpretation.

Detection of the Infusion Line Disconnection

In some instances, the infusion line may become disconnected from the pump and a leakage may occur between the pump outlet and the infusion line connector. Leakage may also be present if the user connects an unapproved infusion line to the pump outlet. This results in a lower fluidic resistance at the pump outlet because of such leakage. The small decrease of pressure at the pump outlet when the leak becomes significant could be detected by using the integrated detector or by placing a second pressure sensor in the micro-pump but after the outlet valve. The sensitivity of this sensor should be adapted to the pressure loss of the infusion line under normal conditions.

The high instantaneous flow rate of the pump due to its functioning principle is very favourable since the pressure drop in the infusion line is directly proportional to the flow rate.

If necessary, a specific test of tightness of the infusion line can be done by generating for instance a stroke at higher speed for the liquid exhaust during the pump setting, preferably before the patient is connected (e.g. during priming of the pump).

Additional Pressure Sensor at the Pump Outlet

The main detector is placed in the pumping chamber. Its reference port is communicating with the air space inside the pump system's housing which is at atmospheric pressure as long as the pump system is well ventilated. This sensor is also a relative pressure sensor. It could be useful to get information about the patient's pressure, by placing an additional pressure sensor after the outlet valve.

This additional pressure sensor is directly related to the patient's pressure. The two pressures sensors, the main one measuring the pressure inside the pumping chamber and the one measuring the pressure after the outlet valve, should have the same reference port pressure. Comparing the evolution of the two signals after a stroke is useful for the detection of leaks within the pump, at the valve seats, or between the outlet port of the pump and the patient (typically a bad connection of the patient set). This will be described in more details further in the present description.

Moreover, the difference of pressure between the two sensors just after the stroke, i.e. when there is no longer flow rate, is also a good indication of the outlet valve tightness.

This additional sensor can be also used for the detection of abnormal pressure at the outlet port, including occlusion of the infusion set.

This additional sensor could also be calibrated if needed during the functional manufacturing testing, using gas as described above in the present specification This additional pressure sensor could be easily integrated into the pump chip by designing a second membrane for the pressure measurement: the pressure can be measured by using strain gauges in a Wheatstone bridge configuration as used for the other pressure sensor inside the pump. Ideally the implantation doses for the strain gauges are the equivalent ones to those of the main detector inside the pump. One can therefore adjust the sensitivity if necessary by simply modifying the membrane dimensions rather than the doses themselves.

The fluidic pathway between the outlet valve of the pump and the patient set should preferably be made not to trap air during the initial pump priming.

Implementation of a Temperature Sensor for a Better Leak and Accuracy Monitoring Using the Additional Pressure Sensor The present section discusses the reliability during the analysis of the second detector signal.

As mentioned previously, the width and the height of the peak of pressure can be exploited in order to get information about the tightness of the downstream line between the pump and the patient. One can also propose qualitative criterions for these different features.

Moreover, the integral of the pressure versus time curve is theoretically proportional to the flow rate, for a given fluidic resistance. A change in this integral is a good indication of a dysfunction, including bubbles, leaks . . . but also temperature changes.

$$P(t)-P(\text{patient})=Rf\times Q(t)$$

Where Rf is the fluidic resistance between the additional pressure sensor and the patient, Q(t) the instantaneous flow rate and P(t) the pressure measured by the additional sensor. Laminar flow is taken into account and Rf is given by the Poiseuille's law. P(patient) is the pressure of the patient and also the pressure measured by the additional sensor after the flow vanishes.

This sensor is also a good indicator for the pumping accuracy since we have a direct access to the flow rate variation with time. Of course, for a given pumping system including the infusion set, the fluidic resistance will vary with temperature via the fluid viscosity (Poiseuille's law). Ideally this pressure sensor will also be coupled to a temperature sensor.

If liquid like water is used, the variation of the viscosity with the temperature is well known and the correction of the signal can be done in order to no longer be temperature dependant. The dysfunction detection becomes now even more reliable.

The temperature sensor could be placed within the pump, for instance in contact with the liquid even if it is strictly not necessary thanks to the small dimensions and good thermal conductivity of the pump components.

The thermal sensor could be a simple thermo-resistor (RTD or resistance temperature detector) that shows a good sensitivity between 5 and 40° C. The Wheatstone bridge of the pressure sensors also shows similar temperature dependence and could serve for this purpose. A thermocouple can also be incorporated in the pumping unit. Finally a semi-conductor temperature sensor based on the fundamental temperature and current characteristics of a diode or a transistor can be used.

If two identical transistors are operated at different but constant collector current densities, then the difference in their base-emitter voltages is proportional to the absolute temperature of the transistors. This voltage difference is then converted to a single ended voltage or a current. An offset may be applied to convert the signal from absolute temperature to Celsius or Fahrenheit.

Figure 13:
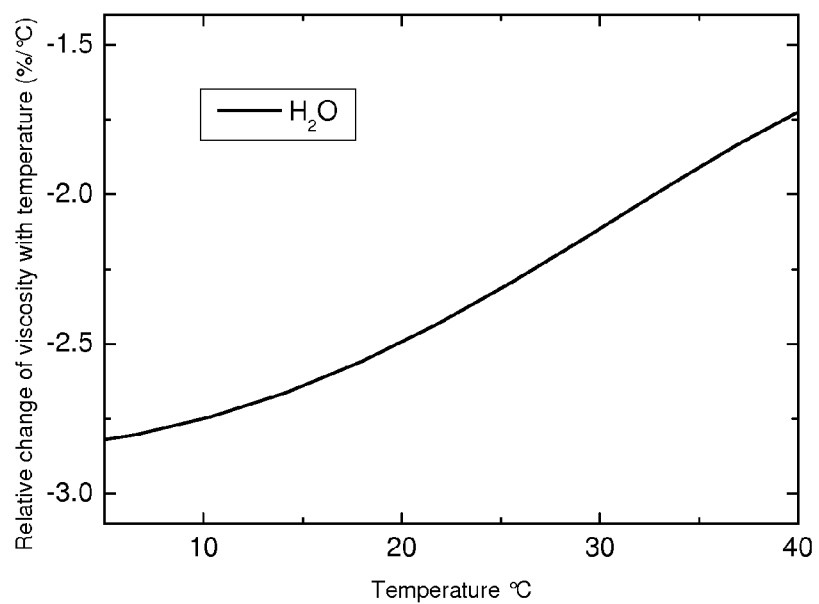
FIG. 13 illustrates the relative variation of viscosity for a temperature change of 1° C.

FIG. 13 shows the relative variation of viscosity for a temperature change of 1° C. Since the fluidic resistance varies linearly with the viscosity, it become possible to directly access to the flow rate accuracy which can be expected for a temperature sensor resolution of 1° C.: at 5° C. the max error induced by the temperature sensor over the flow rate accuracy is 2.8%. The sensor may also be designed in order to introduce an error lower than the accuracy target for the flow rate.

The coupling of the pressure sensor at the outlet and the temperature sensor could be used as a smart relative pulsed flow sensor which is efficient thanks to the small response time of the pressure sensor.

Absolute Flow Meter

For an absolute flow measurement, the fluidic resistance between the additional pressure sensor and the patient should be known with a good accuracy. The patient's set shows typically large variation of fluidic resistance from one batch to another, by contrast to the fluidic resistance of a channel in the micro-pump. Care should also be taken to keep the fluidic resistance of the patient's set very low by contrast to the fluidic resistance of the outlet channels within the micro-pump.

The fluidic resistance Rf given above can be controlled with an accuracy compatible with an absolute flow measurement.

According to the previous discussion, the flow measurement is valid as long as the fluidic resistance of the patient's set remains small, i.e. there is no occlusion of the fluidic line.

The flow rate at the outlet of the micro-pump is measured. Any leakage after the additional pressure sensor (connector . . . ) will induce a change of the signal shape of both detectors, but the flow measured remains correct.

The flow monitoring is also a very powerful feature but we still need information of both detectors for a correct interpretation of the flow data.

During the additional pressure sensor calibration, it is also possible to make a calibration of the integral of the pressure signal which is proportional to the flow rate (typically by using a commercial flow meter placed in series with the outlet of the pump). Here again care should be taken of not introducing a large fluidic resistance at the outlet during the test.

The invention is of course not limited to the examples discussed and illustrated above but cover any embodiment falling under the scope of the claims.

The invention claimed is:

1. A medical pumping system for administering a medical fluid to a patient, the medical pumping system comprising:
   a reservoir storing the medical fluid;
   an infusion line for a fluid connection with the patient at an injection site;
   a pump configured to move the medical fluid through a fluid pathway from the reservoir to the infusion line;
   a first sensor configured to measure a fluid pressure inside the pump;
   a second sensor configured to measure a fluid pressure downstream the pump; and
   a processor configured to process the fluid pressure data received from the first sensor and the second sensor to detect a dysfunction in the infusion line based on the fluid pressure data,
   wherein the medical pumping system is configured to inform the patient of a need to either check the infusion line or change the injection site.

2. The medical pumping system according to claim 1, wherein the medical system is configured to perform a test of the infusion line by generating at least one stroke of the pumping device.

3. The medical pumping system according to claim 1, wherein the dysfunction of the infusion line includes at least one event of the following list: leakage, occlusion, presence of air bubbles, and disconnection.

4. The medical pumping system according to claim 1, wherein the medical fluid is an insulin solution.

5. The medical pumping system according to claim 1, wherein the processor is configured to monitor the pressure profile measured by the first and second sensors.

6. The medical pumping system according to claim 5, wherein the processor is configured to monitor the position of the plateau defined by the pressure profile.

7. The medical pumping system according to claim 5, wherein the processor is configured to monitor the height and/or the width of the peak defined by the pressure profile.

8. The medical pumping system according to claim 1, wherein the processor is configured to analyze the pressure profile measured by the sensor from one stroke to another in order to detect the dysfunction.

9. The medical pumping system according to claim 1, further comprising a ventilated housing which is at the atmospheric pressure,
   wherein the first sensor comprises a relative pressure sensor having a reference port in communication with the air space inside the housing.

10. The medical pumping system according to claim 1, wherein the first sensor and the second sensor comprise a same reference port pressure.

11. The medical pumping system according to claim 1, wherein the processor is configured to compare the evolution of first sensor data and second sensor data.

12. The medical pumping system according to claim 1, wherein the processor is configured to determine the difference of pressure between the first sensor and the second sensor just after a pump stroke.

13. The medical pumping system according to claim 1, further comprising a valve arranged between the first sensor and the second sensor.

* * * * *